United States Patent [19]
Douglas

[11] Patent Number: 5,556,748
[45] Date of Patent: Sep. 17, 1996

[54] METHODS OF SANDWICH HYBRIDIZATION FOR THE QUANTITATIVE ANALYSIS OF OLIGONUCLEOTIDES

[75] Inventor: Allan S. Douglas, Ridgewood, N.J.

[73] Assignee: Xenopore Corporation, Hawthorne, N.J.

[21] Appl. No.: 737,469

[22] Filed: Jul. 30, 1991

[51] Int. Cl.⁶ .................................................. C12Q 1/68
[52] U.S. Cl. ...................... 435/6; 435/7.5; 435/25; 435/27; 435/28; 435/29; 435/34; 435/35; 536/22.1; 536/23.1; 536/24.1; 536/24.3; 536/24.31; 536/24.32; 536/24.33; 935/77; 935/78
[58] Field of Search .................... 435/6, 29, 34, 435/35, 7.94, 25, 28, 7.5; 536/27, 18.7, 23.1, 24.3, 22.1, 23.1, 24.1; 935/2, 16, 19, 24.3-33, 77, 78; 422/56

[56] References Cited

U.S. PATENT DOCUMENTS

| | | | |
|---|---|---|---|
| 4,486,539 | 12/1984 | Ranki et al. | 435/6 |
| 4,563,419 | 1/1986 | Ranki et al. | 435/6 |
| 4,582,810 | 4/1986 | Rosenstein | 436/528 |
| 5,126,241 | 6/1992 | Schenk | 435/7.1 |
| 5,374,524 | 12/1994 | Milles | 435/6 |

FOREIGN PATENT DOCUMENTS

| | | |
|---|---|---|
| 0139489 | 5/1985 | European Pat. Off. |
| 302715 | 6/1989 | European Pat. Off. |

OTHER PUBLICATIONS

Syvanen Medical Biol. 64:313 (1986).
Ranki et al. Gene 21:77 (1983).
Syvanen et al. Nucleic Acids Res. 14(12):5037 (1986).
Urdea et al. Gene 61:253 (1987).

Primary Examiner—W. Gary Jones
Assistant Examiner—Ardin H. Marschel
Attorney, Agent, or Firm—Siegmar Silber

[57] ABSTRACT

The invention is directed to a sandwich hybridization assay wherein a nucleic acid capture probe is firstly immobilized on an assay plate via masked receptors on the plate. The capture probe is immobilized by the binding of receptor ligands on the capture probe during this first step. Subsequently, target nucleic acid is hybridized to the immobilized capture probe either before or after the hybridization of an indicator nucleic acid probe onto the target. The target is quantified via detection of the immobilized indicator signal.

16 Claims, 1 Drawing Sheet

METHODS OF SANDWICH HYBRIDIZATION FOR THE QUANTITATIVE ANALYSIS OF OLIGONUCLEOTIDES

CROSS REFERENCE TO RELATED APPLICATION

This application is related to a commonly assigned, application filed by the same inventor, which application bears Ser. No. 07/720,245 and a filing date of Jun. 24, 1991, now abandoned.

BACKGROUND OF THE INVENTION

1. Field of the Invention

This invention relates to a device for use in the liquid phase quantitative analysis of oligonucleotides, such as deoxyribonucleic acid (DNA) and the method of forming the device. The invention also relates to a DNA assay kit that includes the device and to the method of obtaining quantitative analyses by the use thereof. More particularly, the analysis, in its preferred form, entails using colorimetric techniques.

2. Information Disclosure Statement

In the past, the technology for liquid phase quantitative analysis of oligonucleotides, particularly DNA, has not been available. Most quantitative analysis of DNA has been in the solid phase either through column chromatography or filter media techniques such as the Downs and Wilfinger Method. [Ref. Anal. Blochem., 131, pp. 538–47 (1983).]

DNA molecules are double stranded helical molecules. Each strand consists of sequences of nucleic acids held together by phosphate linkages. The sequence of nucleotides determines the function of the molecule. The two strands are held together by base pair complementary binding, and each strand of DNA binds only to its complement. By using the proper conditions of pH and temperature, it is possible to split the double strand into two complementary single strands. The single stranded DNA can be used to identify the source of a particular material by comparing the sequence of nucleic acids with the sequence from known sources. Alternatively, the presence of a particular DNA can be detected by attempting to hybridize it to a complementary DNA of known sequence.

Most DNA analysis is carried out by hybridization studies on a membrane surface. In this technique, the DNA to be identified is immobilized onto the surface of a nitro cellulose membrane by spotting a drop of solution containing the single stranded DNA onto the membrane, sealing the membrane into a plastic bag and incubating overnight at elevated temperatures. Then a solution of the complementary DNA which has been tagged with radioactive $I^{125}$ or $p^{32}$ is placed onto the spot and incubated again to allow hybridization to take place. After incubation, the spot is washed carefully to remove any unbound material, and then the presence of radioactivity is measured. If the unknown strand and the radio labelled strand are complementary, radioactivity will be retained. The success of the procedure requires that the binding conditions and the hybridization condition be different enough to prevent any direct binding of the labelled DNA to the membrane. This procedure is at best a semi-quantitative procedure, and in most cases is only qualitative because the area of the spot is not confined and well defined.

In preparing for this application, a search of the Chemical Abstracts was conducted. This search uncovered the following:

PCT Int'l. Appl.—WO 90 07582, Jul. 12, 1990, U.S. Appl. Ser. No.—293,895; PCT Int'l. Appl.—WO 88 02785, U.S. Appl. Ser. No.—919,201; and, an article by J. Lundeberg et al, entitled "Rapid Colorimetric Detection of In Vitro Amplified DNA Sequences" from DNA And Cell Biology, Vol. 9, No. 4, 1990. These references are of interest only.

In further preparation, a pre-examination patentability search was performed, which search reviewed several subclasses of Class 935, especially Subclasses 78 and 86. The search uncovered the following patents:

U.S. Pat. No. 4,767,699—C.P.H. Vary et al. (Allied Corp.)

The probe described contains biotin, and the hybridized complex may be separated therefrom using a streptavidin-bound matrix. The probe therefrom is bound covalently or otherwise to a solid support: this may include binding with a biotin-avidin or streptavidin bridge.

U.S. Pat. No. 4,889,798—E. Rabbani (Enzo Blochem Inc.) This patent describes a heterologous detection system for a biotinylated probe. The probe can be fixed to nitrocellulose paper, nylon, etc.

U.S. Pat. Nos. 4,751,177 4,797,355—Y. Stabinsky (Amgen Inc.)

A polynucleotide is synthesized on a solid support such as glass, and is then used for binding polynucleotide probes. (The glass described is amine-functionalized with a silane derivative).

U.S. Pat. No. 4.994,373—J. G. Stavrianopoulos et al. (Enzo Blochem, Inc.)

Polynucleotide sequences to a glass support, which may have wells, e.g. by using ganuna-aminoproply-triethoxysilane. Biotin-avidin may be used to bond a signalling moiety to the probe.

U.S. Pat. No. 4,886,741—D. E. Schwartz (Microprobe Corp.)

Enzymatic detection of hybridized probes using biotin with an enzyme conjugated with avidin or streptavidin is discussed.

U.S. Pat. No. 4,888,274—C. M. Radding et al. (Yale University)

Biotinylated probes and target purification by streptavidin chromatography are described in examples.

U.S. Pat. No. 4,925,785—C.-N. J. Wang et al. (Biotechnica Diag. Inc.) Hybridization methods using a solid support bound to a nucleic acid sequence which can bond to a probe. In a heterogenous sandwich assay, a polymer-bound probe is restricted to a very small area on the support, to increase signal intensity from the label.

U.S. Pat. No. 4,908,307—K. D. Rodland et al.

Variants of conventional hybridization of DNA bound to nitrocellulose or nylon membranes are disclosed. Labeling by biotinylated adenosine polymer and detection using streptavidin and biotinylated enzyme are mentioned.

These patents are a typical reflection of the state-of-the-art of genetic engineering assay procedures, but do not generally reflect the application of the same to liquid phase systems or to quantitative analysis of oligonucleotides. These patents do not provide a means for nor do they teach toward forming or using a masked receptor as described hereinbelow or for the method of use thereof.

Further, the typical reflection of the state-of-the-art of immunoassay procedure, specifically as to covalent binding, is attained by reference to U.S. Pat. No. 4,778,767. There it is noted that Shekarchi, et al., J. Clin. Microbiology 16(6), 1012–1018 (December, 1982) discloses an immunoassay procedure wherein an immunoreagent is immobilized on a small stick, i.e., "microstick", for easy manipulation of the reagent and the immunocomplex. While a number of materials were investigated for use in such microsticks, including stainless steel, nylon, polycarbonate, polystyrene and polytetrafluoroethylene (PTFE), it was found that the PTFE, cleaned by the conventional procedure of rinsing with 6N HCl, absorbed very little of the immunoreagent as compared with the other materials and could not be used as a base for the immunoreagent until it had been coated with polycarbonate or nitrocellulose. The previously referenced patent further cites German Offenlegungsschrift No. 32 00 822, published Jul. 21, 1983, which discloses a method for activating the surface of PTFE articles, in order to bond immunoreagents covalently, by contacting the PTFE surface with an ammoniacal solution of sodium, followed by treatment with carbodiimide. It indicates that the process was apparently attempted because it was found that adsorption of the immunoreagent on PTFE was unsatisfactory, and also that there is some question whether the procedure of this German application actually can immobilize a useful amount of immunoreagent on PTFE. As are described in more detail below, other procedures for surface treatment of polystyrene have been adopted resulting in the commercial availability of polystyrene covalent binding plates.

In addition to the Syvanen et al. reference cited in the U.S. Application, an International Search Report of the corresponding application has brought to the inventor's attention the following:

EPA 0 390 500—David Okrongly (Applied Immunesciences, Inc.)

The publication describes the covalent attachment of macromolecules on substrate surfaces, particularly uncrosslinked polystyrene. The surface is functionalized employing hydroxymethylamides and is then useful for complex formation between complementary binding pairs.

WO A 8 607 387—David L. Snitman et al. (Amgen)

This publication describes a kit for the isolation and detection of a selected target nucleic acid sequence. A solution hybridization with two probes, each complementary to a different portion of the target. After hybridization of the target, a solid support is employed to immobilize the target-probe hybrid complex.

EPA 0 192 168—Nanibrushan Dattagupta (Molecular Diagnostics, Inc.)

This publication describes assay method for detecting the presence of a particular polynucleotide sequence in a test sample. After solution hybridization, the target probe hybrid is bound to an immobilized form of the reaction partner. The detection probe is labeled as desired.

In the field of oligonucleotide assays, the need for liquid phase, quantitative analysis has been a long-standing problem which is addressed by this invention.

SUMMARY

In general terms, the invention disclosed hereby includes in the apparatus embodiment thereof, an assay device for quantitative liquid-phase analysis of an oligonucleotide, such as deoxyribonucleic acid (DNA) that consists of a plastic base, typically polystyrene; covalent binding means for covalent bonding of-receptor materials to the surface of the base utilized in the assay, said means being a surface modification to produce covalent binding sites integral with the plastic base material; a receptor agent (avidin, streptavidin, monoclonal antibody directed against sulfonated DNA, etc.) forming sites thereof by bonding to portions of said binding means and forming interstices therebetween; and, a mask of, for example, bovine serum albumin with salmon sperm DNA, covering the exposed interstitial portions of the covalent binding means; whereby, upon a presensitized DNA probe with the DNA material-to-be-assayed being adhered thereto, the quantity of DNA is determinable by colorimetric, fluorescent or radiometric means.

OBJECT AND FEATURES OF THE INVENTION

It is an object of the present invention to provide a liquid phase quantitative analysis for oligonucleotides, particularly DNA.

It is a further object of the present invention to provide such an analysis using colorimetric technique.

It is yet another object of the present invention to provide a such analysis with assay devices adapting the technique to a microtiter plate format.

It is still yet another object of the present invention to provide such analysis with devices that maintain optical integrity.

It is a feature of the present invention that the assay device has masked receptor sites.

It is another feature of the present invention to provide an assay kit which includes all the materials required for the liquid phase quantitative analysis of DNA.

It is yet another feature of the present invention to provide a calibration between the colorimetric reading and the quantity of the oligonucleotide present.

Other objects and features of the invention will become apparent upon review of the drawings and the detailed description which follow.

BRIEF DESCRIPTION OF THE DRAWINGS

In the following drawings, the same parts in the various views are afforded the same reference designators.

DESCRIPTION OF THE PREFERRED EMBODIMENT

In general terms and in the preferred form of the disclosure, an enzyme-linked oligonucleotide assay is described. This assay, generally referred to by the assignee's trademark "ELONA", provides a new microwell-plate based assay for quantitative determination of the concentration of a specific target DNA. The process is based in part on covalent bonding technology, referred to in the Information Disclosure Statement, and in part on the modification of plastic surfaces as presently commercially available. Although the Xenopore plate is preferred, as will be seen in more detail below, there are several alternatives available to overcome the problem of DNA not adhering passively to plastic surfaces. In the assay at hand, the covalent binding property of the plate enables the production of receptor sites.

In the description which follows, a device is provided for assay purposes and a general regimen of the use of the device in a liquid phase quantitative analysis is provided.

This regimen is first described in terms of a probe sensitization mechanism and of the binding of the sensitized probe to the device of this invention. Then, the material-to-be-assayed or target DNA is introduced onto the device, and, for colorimetric processing, a reaction is initiated and arrested with the optical density reading providing an equivalent quantification of the target DNA. Although the text hereof is prepared for one skilled in analytical work of this nature, from time-to-time definitions are provided to lend clarity to the text and the claims appended hereto.

Figure 1:
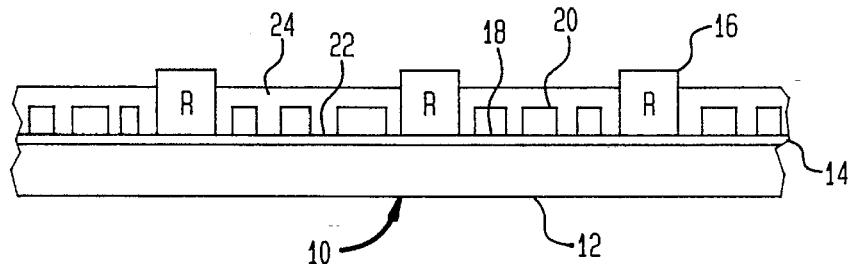
FIG. 1 is a schematic representation of the assay plate of the present invention.

Referring now to FIG. 1, the assay device is shown and is referred to generally by the reference numeral 10. Although in the description of the best mode of this invention, a microtiter or microwell plate format is shown. The assay device is described in terms of a nonformatted container or plate.

A plastic base or plate 12 is constructed to contain a surface layer 14 on a predetermined portion thereof which has been treated for covalent binding. Such treated plates are commercially available from Costar, Inc., Cambridge, Mass—Product Nos. 3390 and 3490; Nunc A/S, Roskilde, Denmark—Product No. 478042; and Xenopore Corp., Saddle Brook, N.J.—Xenobind Plate, Model No. XPL 050 00. Although the bases or plates are most commonly manufactured from polystyrene, other materials such as nylon, polycarbonate, polymethylmethacrylate, polytetrafluoroethylene (PTFE) and polyurethane may be used. In the preferred format employed herein, enzymatic color reactions are used to quantitate the oligonucleotide present in the analyte, and polystyrene has shown to be the material of choice, especially with the plate readers employed. Further, while the microtiter or microwell plates are discussed as preferred, the receptor binding and masking thereof, described in detail hereinbelow, can be constructed on a base of polystyrene beads, including engineered particulate beads having channeling therewithin for enhanced high performance liquid chromatography, such beads are described in the patent to F. E. Regnier et al, U.S. Pat. No. 5,019,270. A receptor 16 is next bound to the surface layer 14 by the method described hereinbelow. The receptor 16 is a glycoprotein typically selected from avidin, streptavidin and a monoclonal antibody against sulfonated DNA. After binding of the receptor 16, the plate 12 is washed to remove any unbound material. At this stage of construction, the receptor material 16 is disposed upon and covalently bound to the treated predetermined portions of surface layer 14 and, among the deposited receptor material 16, interstices or interstitial areas 18 of the surface layer 14 treated for covalent binding remains uncovered. Next a mask material is applied to cover the interstitial areas 18 and, in the preferred form, a coarse and a fine coat are applied or, in other terms, a prime and a finish coat. It is not inconceivable that a "one-shot" application of mask material may be used. In the best mode of practicing this invention, proteinaceous masks are constructed. A primary layer or mask 20 is constructed to cover substantially the interstitial areas 18. Here the preference is for bovine serum albumin which, after removing the excess thereof, being a coarse material is found to yet leave uncovered extremely small interstices or interstitial areas 22. So as to preclude covalent attraction of the analyte, these small interstitial areas 22 also need to be covered. The covering of the interstitial areas 18 is performed with a material which does not interfere with the functioning of the receptor 16. A secondary layer or mask 24 is constructed to cover substantially the interstitial areas 22. Here the preference is for salmon sperm DNA which, after removing the excess thereof, is found to seal completely the yet uncovered surface so that no surface treated for covalent binding remains exposed. The covering of the small interstitial areas 22 is also performed with a material which does not interfere with the receptor 16.

With the above-described assay device, it is seen that the basis of the invention is the ability to covalently attach streptavidin or the receptor of choice to the surface of microtiter plates. While the covalent attachment is most conveniently done by incubation of a solution of streptavidin in carbonate buffer with a Xenobind plate, a microtiter plate having covalent attachment sites on its surface, as indicated, any other compatible covalent binding vehicle may be used. With the assay plate prepared, the use thereof for an oligonucleotide assay is next described.

In the description of the procedures which follow there is no claim made to the hybridization aspects thereof as all of the underlying technology is well within the state-of-the-art. The known complementary oligonucleotides to the oligonucleotide to be detected (hereinafter DNA, by way of example) is reacted with biotin to produce a DNA molecule with biotin binding sites within it. These biotin binding sites are capable of reacting with streptavidin to form a strong stable bond. In the most preferred procedure, only one biotin molecule is attached to each DNA molecule, but this is not an essential part of the process. To carry out the detection, the biotinylated complement is treated in either of two ways:

In the first way, the biotinylated DNA complement is mixed with the DNA to be identified and hybridization takes place. The solution is then placed in the wells of a streptavidin coated plate where competitive binding takes place, with the hybridized and non-hybridized biotin containing DNA bind in proportion to their relative concentrations in solution.

In the second way, the biotinylated DNA is placed into the streptavidin coated well and binds to the streptavidin. The DNA to be identified is then added to the well where hybridization takes place. This procedure has the disadvantage of being slower than the first procedure since the DNA complement is partly immobilized but avoids the concentration limitation of the competitive assays.

In either case, after hybridization and binding is completed, and unbound material washed out of the wells, a second, tagged, complement to a different section of the DNA to be identified, is added, and hybridization again occurs. The known DNA fragments in each case are shorter than the DNA to be identified, but long enough to be specific for the molecule to be identified.

Any one of a number of tags can be used for identification. If the first probe has only single biotin molecule, such that there are no free biotins, then the second probe can also be biotinylated. Then an avidin-alkaline phosphatase complex can be bound to be immobilized material and the color developed with an appropriate substrate. The intensity of color depends on the quantity of DNA (the target) present in the solutions and appropriate calibration produces quantitative results.

Another detection system uses a sulfonated DNA as the second probe and a monoclonal antibody specific for sulfonated DNA is added, followed by an alkaline phosphatase tagged polyclonal anti-antibody.

A third detection system involves tagging the DNA with a luminous material which is activated by a substrate and can be quantitated.

Detailed Procedure

In the detailed procedures which follow, numerous buffers are used at various stages of the assay. It is within the state-of-the-art to substitute variations of the buffers without changing the invention hereof, and thus it is indicated that a "suitable buffer" may be used. For purposes of this disclosure, a "suitable buffer" for the covalent binding step is defined as a buffer in which the pH thereof is above the isoelectric point of the protein being bound. A "suitable buffer" for the hybridization step is any buffer in which the DNA retains its ability to hybridize. The buffers are referred to by their standard abbreviations as given in the "Information for Contributors" in The Journal of Immunology: the Official Journal of The American Association of Immunologists. The hybridization and immunoassay procedures referred to in this disclosure are described in detail in the book, Biochemistry, 3rd edition, by Lubert Stryker (W. H. Freeman and Company, New York, 1990). It is also noted that various enzyme conjugates can be linked to the second polynucleotide probe according to the parameters at hand. Some of the commercially available enzyme systems include:

Avidin Related Enzyme System

Avidin
  Unit Definition: One unit will bind 1.0 µg of d-biotin.
Avidin-Alkaline Phosphatase Labeled (Sigma A2527)
  Labeled with Type VII alkaline phosphatase, lyophilized powder containing approx. 35% protein (Warburg-Christian); balance primarily Tris aspartate buffer with trace magnesium acetate and zinc sulfate. Contains 1–3 moles of alkaline phosphatase per mole of avidin. Actual content given on label.
Avidin Activity
  2–6 units per mg protein.
Alkaline Phosphatase Activity
  300–500 units per mg protein. Unit Definition: One unit will hydrolyze 1.0 µmole of p-nitrophenyl phosphate per min at pH 10.4 at 37° C.
Avidin, 2, 3-Dihydroxypropylfluorescein Isothiocyanate (Sigma A8409)
  Lyophilized powder containing approx. 90% protein; balance primarily sodium citrate buffer salts. Contains approx. 3 moles FITC per mole hydroxypropyl avidin.
Avidin-Ferritin Labeled (Sigma A5405)
  Lyophilized powder. Approx. 30% protein; balance primarily tris buffer salt. Labeled with equine spleen ferritin. Actual ferritin to avidin ratio given on label.
Avidin-FITC Labeled (Sigma A2901)
  Lyophilized powder containing approx. 80% protein ($A_{280}$); balance primarily sodium citrate. Approx. 3 moles of fluorescein isothiocyanate per mole of avidin.
Avidin Galactosidase Labeled (Sigma A2930)
  Lyophilized powder containing approx. 50% protein ($E_{280}^{1\%}$); balance primarily Tris-succinate with a trace of dithiothreitol. Prepared from avidin (A 9275), partially acetylated, and β-galactosidase (G 5635). Contains 1–3 moles avidin per mole galactosidase.
Galactosidase Activity
  100–400 units per mg protein.
Avidin Activity
  2–4 units per mg protein.
  Unit Definition: One unit will hydrolyze 1.0 µmole of o-nitrophenyl β-galactoside per min, at pH 7.3 at 37° C.
Avidin-Peroxidase Labeled (Sigma A3151)
  Labeled with Type VI peroxidase. Lyophilized powder containing approx. 80% protein ($E_{280}^{1\%}$); balance primarily citrate buffer. Contains 0.7–2.0 moles peroxidase per mole avidin.
Avidin Activity
  5–10 units per mg protein.
Peroxidase Activity
  50–150 units per mg protein.
  Unit Definition: One unit will form 1 mg of purpurogallin in 20 sec from pyrogallol at pH 6.0 at 20° C.
Avidin-Rhodamine Isothiocyanate Labeled (Sigma A3026)
  Lyophilized powder containing approx. 90% protein (Biuret); balance primarily citrate buffer salts. Contains 1–2 moles of rhodamine isothiocyanate per mole of avidin.
Avidin, Succinylfluorescein Isothiocyanate (Sigma A8534)
  Lyophilized powder containing approx. 90% protein (Biuret); balance primarily sodium citrate buffer salts. Contains 2–4 moles FITC per mole succinyl-avidin.
Avidin, Succinyl-Gold Labeled
  Avidin (Sigma A 9275), succinylated to reduce nonspecific interaction, adsorbed to colloidal gold for detection of biotinylated compounds. Suspension in 50% glycerol containing 0.01M Tris buffer, 0.15M NaCl, 0.02% PEG 20 and 0.02% sodium azide, pH, 7.0.
Concentration
  $A_{520}$ approx. 5.0

Having described the choices of enzyme conjugates available, the detailed procedure is now set forth for a DNA analysis.

A. Covalently bind receptor to plate surface.
  1. Prepare a solution of 3 µg/ml of avidin or streptavidin in carbonate buffer at pH-9.6. Add to wells;
  2. Incubate for three hours at 37° Centigrade or overnight at room temperature; and,
  3. Wash plate with tris buffer or phosphate buffer 3 times to remove unbound material.
B. Block unreacted sites.
  1. Prepare a solution of 3% BSA in PBS buffer pH=7.2;
  2. Add to wells and incubate for 3 hours at 37° or overnight at room temperature.
  3. Wash three times with PBS buffer to remove unbound material;
  4. Prepare a solution of 500 µg/ml of denatured salmon sperm DNA in 10×SSC buffer;
  5. Add to wells and incubate 3 hours at 37°; and,
  6. Wash 3 times with 10×SSC buffer to remove unbound material.
3. Prepare the sensitized 1st probe.
  1. React the oligonucleotide complement to the target DNA with the appropriate biotinylating reagent such as photobiotin.
4. React the sensitized probe to the prepared blocked plate.
  1. Transfer the sensitized probe to PBS buffer at 3 µg/ml concentration;
  2. Add to wells and incubate 30 minutes at room temperature; and,
  3. Wash three times with PBS buffer to remove unreacted probe.
5. Hybridize the target.
  1. Add solution containing the target DNA to the wells and react for 1 hours at 37°; and,
  2. Wash 3 times with PBS to remove unreacted material.
6. Block the unreacted biotin.
  1. Prepare a solution of 3 µg/ml of streptavidin in PBS;
  2. Add to the wells and incubate for 30 minutes at room temperature. This blocks any biotin sites that have not reacted with streptavidin on the plates; and,
  3. Wash wells three times with PBS to remove unreacted material.

7. Prepare the sensitized second probe.
    1. Repeat step 3 with the complement to another section of the target DNA.
8. React the 2nd probe to the immobilized target.
    1. Transfer the sensitized probe to PBS buffer at 3 μg/ml concentration;
    2. Add to the wells and incubate for 30 minutes at room temperature.
    3. Wash 3 times with PBS to remove unreacted material.
9. Add the detection system.
    1. Prepare a solution of avidin-alkaline phosphatase conjugate in PBS at 3 μg/ml;
    2. Add to the wells and allow to react for 30 minutes at room temperature;
    3. Wash 3 times with PBS to remove unreacted material;
    4. Add substrate (nitrophenyl phosphate); and,
    5. Stop reaction after color develops with NaOH.
10. Read the results with a standard plate reader.

Alternate Procedure

Steps 1–3 same as above.
4. Hybridization.
1. Mix the sensitized probe with the solution containing the target DNA. Allow to hybridize for 30 minutes; and,
2. Add the solution to the wells; the avidin-biotin reaction will occur, immobilizing the hybridization product to the plate.
Continue with Step 6 above.

Second Alternate Procedure

Steps 1–5 same as above.
6. Omit
7. Prepare the sensitized second probe.
    1. Sulfonate the DNA;
    2. Transfer to 10×SSC buffer at 1 μg/ml concentration.
8. React the second probe to the immobilized target.
    1. Add to the wells and allow hybridization to occur for minutes at 37°;
    2. Wash 3 times with PBS to remove unreacted material.
9. Add the detection system.
    1. Add the monoclonal antibody to sulfonated DNA at a concentration of 1 μg/ml;
    2. Allow to react 1 hour at 37°;
    3. Wash 3 times with PBS to remove unreacted material;
    4. Add polyclonal antibody-alkaline phosphatase conjugate directed against the monoclonal antibody;
    5. Allow to react for 1 hour at 37°;
    6. Wash 3 times with PBS to remove unreacted material;
    7. Add substrate (nitrophenyl phosphate); and,
    8. Stop reaction after color develops with NaOH.
10. Read the results with a standard plate reader.
Other variations
1. Use the monoclonal on the plate, sulfonate the first probe and use the avidin-biotin detection system;
2. Use horseradish peroxidase as the enzyme with an appropriate substrate;
3. Use another sensitizer-receptor system with either avidin-biotin detection, sulfonated monoclonal detection and any suitable enzyme-substrate combination; and,
4. Use a radioactive or fluorescent detection system or a luminescent detection system.

Method of Liquid Phase Quantitative Analysis

Figure 2:
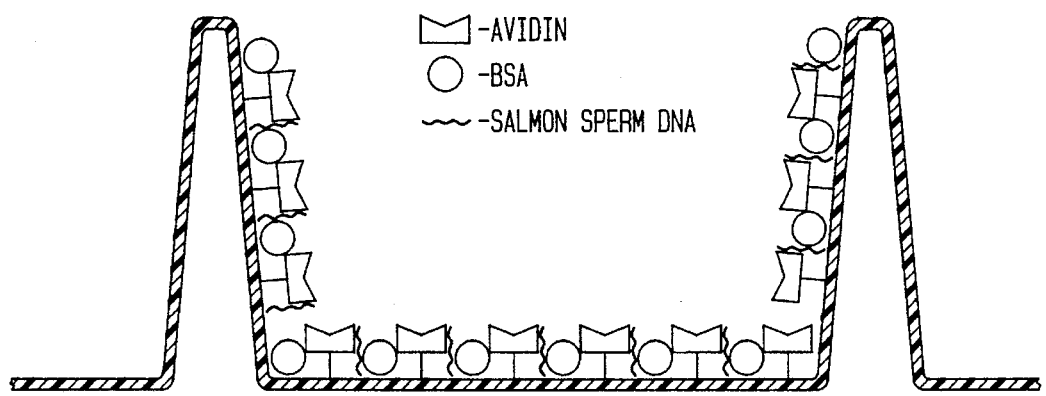
FIG. 2 is a schematic representation of the assay device shown in a microwell format, said schematic representation using symbols explained therein; and, FIG. 3 is a schematic representation of the enzyme linked oligonucleotide assay of the present invention.
Figure 3:
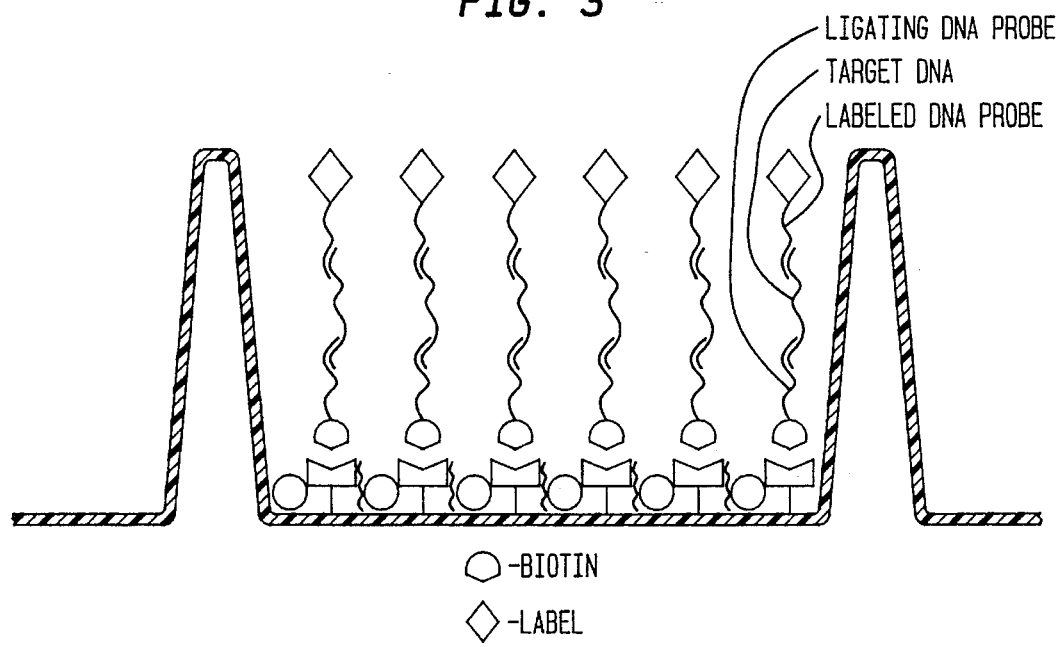

Referring now to FIGS. 2 and 3, an assay plate prepared with masked receptor sites as described hereinabove is used for liquid phase quantitative analysis by the following steps:

1. sensitizing a ligating polynucleotide (DNA) probe, said ligating DNA probe being complementary to a first portion of the target oligonucleotide and being attachable to the receptor site;
2. attaching the ligating DNA probe to the receptor sites;
3. hybridizing the denatured target oligonucleotide to the complementary portion of the ligating DNA probe;
4. labeling a polynucleotide (DNA) probe with an enzyme conjugate and thereby forming a labeled DNA probe, said labeled DNA probe being complementary to a second portion of the target oligonucleotide;
5. hybridizing the denatured target oligonucleotide to the complementary portion of the labeled DNA probe;
6. adding a substrate to react with the enzyme conjugate of the labeled DNA probe and then a reagent to fix the label development at a desired point;
7. reading the intensity of the label and calibrating the readout to indicate the quantity of target oligonucleotide present.

With the steps of the quantitative analysis method generally set forth above, the various steps are now elaborated by reference to the Detailed Procedure and the schematic diagrams. Where the first or ligating probe is used with an avidin or streptavidin receptor, the probe is biotinylated by the procedure hereinabove provided. Where the first or ligating probe is used with a receptor of a monoclonal antibody against sulfonated DNA, the DNA probe is treated correspondingly by sulfonation. Referring to the schematic diagrams of FIG. 2 and FIG. 3, the exemplary avidin receptor sites are shown with the masking layers thereabout. In FIG. 3, attention is drawn to the first probe with the biotin portion thereof attached to the avidin receptor; to the first probe with the complementary portion of the target DNA; and to the second probe with the complementary portion thereof hybridized to the second complementary portion of the target DNA. The schematic diagram also shows the labeling enzyme conjugate attached to the second probe. Here, the example of an avidin-alkaline phosphatase conjugate and a nitrophenyl phosphate substrate is used. Any of a variety of microwell plate readers are commercially available. Typical of the instruments available is the Sigma Chemical Co. Bichromatic Photometer, Catalog No. M6280, a microwell plate reader for enzyme immunoassay testing. This instrument may be used with any microwell plate.

EXAMPLES

Examples for the purposes of this invention are provided hereinbelow:

Example 1

Preparation of Streptavidin Coated Plate

A solution of 3 μg/ml. of streptavidin in carbonate buffer (pH=9.6) was placed in the wells of a Xenobind Covalent Binding Plate (Cat. No. XPL 050 00) and incubated for 3 hours at 37° C. The plate was then washed 3 times with PBS buffer (pH=7.0) and then incubated 3 hours with a 3% BSA in PBS solution (pH=7.0) at 37° C. The plate was then washed 3 times with PBS (pH=7.0) to remove any unbound BSA. The plate was next incubated for two hours with a solution of 500 μg/ml of denatured salmon sperm DNA in 10×SSC at room temperature. The plate was washed three times with 10×SSC to remove unbound DNA. The plate was tested for unblocked binding sites by reacting it with a solution of 3 μg/ml of avidin-alkaline phosphatase for three hours at 37° C. and then washed three times with PBS buffer. A 10 mM solution of p-nitrophenyl phosphate was incubated in the wells for 2 hours at 37° C. No color developed, indicating that there were no unblocked sites. A second plate was tested with a sulfonated DNA prepared from one fragment of a HindIII digest using the Sigma Chem-Probe kit. The plate was then reacted with a monoclonal antibody to sulfonated DNA, a polyclonal antibody to the monoclonal conjugated to alkaline phosphatase and after washing with PBS 3 times, with a 10 mM salution of p-nitrophenyl phosphate. No color developed.

Example 2

A prepared blocked plate was reacted with a biotinylated Hind III DNA probe (0.05 μg/ml in 10×SSC) for 1 hour at room temperature and then washed three times with 10×SSC. The complementary DNA (0.1 μg/ml) was added as the target and hybridized for 1 hour at 42° C. and then washed three times with 10×SSC to remove unhybridized DNA. A sulfonated Hind III DNA fragment, complementary to the target was hybridized at 42° for one hour and then the plate was washed 3 times with 10×SSC. The plate was then reacted with the monoclonal-polyclonal antibody system described in example one and the color was developed with p-NPP. The optical density was measured on a standard plate reader at 405 nm. The OD was 0.150.

Example 3

A prepared blocked plate was reacted as in example 2, but the target concentration was 0.15 μg/ml. The OD was 0.223.

Example 4

A prepared blocked plate was reacted with a biotinylated plasmid DNA PUC 119 at 0.05 μg/ml in 10×SSC for 1 hour at room temperature. After washing 3 times with 10×SSC it was reacted with a complementary plasmid DNA at 1 μg/ml in 10×SSC at 42° C. for 1 hour. The plate was washed again three times with 10×SSC and then reacted with a second biotinylated plasmid probe at 0.1 μg/ml for 1 hour at 42° C. The plate was washed again with 10×SSC and then incubated with avidin-alkaline phosphatase conjugate (0.2 μg/ml in blocking buffer) for 30 minutes at room temperature. The unbound conjugate was washed from the plate and the color developed with 10 mM p-nitrophenyl phosphate for 30 minutes at 37° C. The color was measured at 405 nm on a standard plate reader. The OD was 1.8.

Assay Kits

The present invention lends itself readily to the preparation of kits having ELONA microwell plates or similar devices and the necessary buffers and reagents for oligonucleotide liquid phase quantitative analysis. A kit can contain the components required to biotinylate the oligonucleotide probe. Also, the kits can contain the components required after the probe is attached to the plate and to the target oligonucleotide, for labelling the second DNA probe developing the color, and arresting color development.

The ELONA kit includes a microwell plate with streptavidin covalently attached to the surface thereof and the streptavidin is suitably masked to eliminate the binding of unwanted material directly to the interstitial areas of the plate. Thus there are no random, unmasked sites for the covalent binding of protein or DNA.

A researcher scientist will have all the components needed to carry out the assay. The Xenoprobe ELONA kit contains an avidin coated blocked plate, biotinylating reagent, streptavidin, streptavidin-alkaline phosphatase conjugate, substrate, and stopping solution.

A diagnostic test manufacturer can supply the probes already biotinylated with the first probe already reacted to the plate and with the unused biotin sites already blocked. The user has only to add his sample and the second probe, followed by the enzyme conjugate and substrate to obtain a quantitative measure of the concentration of the specific DNA in the sample.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A method of quantitative analysis of an oligonucleotide analyte, said analysis using an assay plate prepared with masked receptor sites and two sensitized polynucleotide DNA probes, each having a different sequence complementary to the analyte comprising performing the hereinbelow steps in the order presented:

(a) attaching the first DNA probe to the receptor sites;

(b) then performing the following two substeps in any order, that is sequentially or in reverse order:

(1) hybridizing the oligonucleotide analyte to the complementary portions of the first and second DNA probes; and, (2) labeling by the attachment of an indicator to the second DNA probe; and, (c) detecting the intensity of the indicator and thereby obtaining a quantitation of said oligonucleotide analyte.

2. A method as described in claim 1 wherein the assay plate thereof is a microwell plate and wherein said labeling is by enzymatically reacting said indicator with a substrate, said reacting of indicator and substrate yielding enzymatic reaction products that are detectable by colorimetric techniques.

3. A method as described in claim 2 wherein the step of attaching of the first DNA probe, includes the following substeps:

(a) transferring the first DNA probe to PBS buffer at 3 μg/ml concentration;

(b) incubating 30 minutes at room temperature; and, (c) washing with PBS buffer to remove unreacted ligating DNA probe materials.

4. A method as described in claim 2 wherein the step of hybridizing the oligonucleotide analyte, includes the following substeps:

(a) adding the solution containing the oligonucleotide analyte to the wells;

(b) transferring the ligating DNA probe at a concentration of 3 μg/ml to phosphate buffered saline (PBS) buffer;

(c) reacting for 1 hour at 37°; and, (d) washing with PBS buffer to remove unreacted material;

(e) blocking the unreacted biotin with a solution of 3 µg/ml of avidin in PBS buffer; and, (f) incubating for 30 minutes at room temperature and washing with PBS buffer to remove unreacted material.

5. A method as described in claim 2 wherein the step of reacting the enzyme conjugate, includes the following substeps:

(a) preparing a solution of avidin-alkaline phosphatase conjugate in PBS buffer at 3 µg/ml;

(b) adding the solution of substep a. and reacting for 30 minutes at room temperature;

(c) washing with PBS buffer to remove unreacted material;

(d) adding a substrate of nitrophenyl phosphate to the reacted conjugate; and, (e) arresting the reaction after color develops with sodium hydroxide.

6. A method as described in claim 5 wherein the detecting of the concentration of the enzymatic reaction products is by a microwell plate reader providing an indication of the optical density of the solution in the microwell.

7. A method as described in claim 6 wherein the microwell plate reader is calibrated to provide directly the quantity of oligonucleotide analyte present.

8. A method of quantitative analysis of a oligonucleotide analyte, said analysis using an assay plate prepared with masked receptor sites, a polynucleotide DNA probe-for-ligation, and a DNA probe-for-detection comprising performing the hereinbelow steps in the order presented:

(a) reacting the DNA probe-for-ligation for the binding thereof, said ligating DNA probe being complementary to a first portion of the oligonucleotide analyte and, upon reaction thereof, being bindable to the receptor site;

(b) attaching the reacted DNA probe-for-ligation, hereinafter the ligating DNA probe to the receptor sites;

(c) hybridizing the oligonucleotide analyte to the complementary portion of the attached ligating DNA probe;

(d) labeling said DNA probe-for-detection by attaching an enzyme thereto thereby forming an enzyme conjugate, said DNA probe hereinafter said detecting DNA probe, detecting DNA probe-for-detection, being complementary to a second portion of the oligonucleotide analyte;

(e) hybridizing the oligonucleotide analyte to the complementary portion of the detecting DNA probe;

(f) adding a substrate to react with the enzyme conjugate of the detecting DNA probe and then a reagent to arrest the enzymatic reaction at a preselected time point;

(g) detecting the concentration of the enzymatic reaction products at the desired end point; and, (h) calibrating the detected concentration to indicate the quantity of oligonucleotide analyte present.

9. A method as described in claim 8 wherein reacting of the ligating DNA probe is by biotinylating thereof.

10. A method as described in claim 8 wherein the assay plate thereof is a microwell plate and wherein the enzyme conjugate is detectable by colorimetric techniques.

11. A method as described in claim 10 wherein the step of attaching of the ligating DNA probe, includes the following substeps:

(a) transferring the ligating DNA probe to PBS buffer at 3 µg/ml concentration;

(b) incubating 30 minutes at room temperature; and, (c) washing with PBS bufer to remove unreacted ligating DNA probe materials.

12. A method as described in claim 10 wherein the step of hybridizing the denatured oligonucleotide, includes the following Substeps:

(a) adding the solution containing the oligonucleotide analyte to the wells;

(b) reacting for 1 hour at 37°; and, (c) washing with PBS buffer to remove unreacted material;

(d) blocking the unreacted biotin with a solution of 3 µg/ml of avidin in PBS buffer; and, (e) incubating for 30 minutes at room temperature and washing with phosphate buffered saline (PBS) buffer to remove unreacted material.

13. A method as described in claim 10 wherein the step of hybridizing the labeled DNA probe, includes the following substeps:

(a) transferring the ligating DNA probe to phosphate buffered saline (PBS) buffer at 3 µg/ml concentration;

(b) incubating 30 minutes at room temperature; and, (c) washing with PBS buffer to remove unreacted ligating DNA probe materials.

14. A method as described in claim 10 wherein the step of reacting the enzyme conjugate, includes the following substeps:

(a) preparing a solution of avidin-alkaline phosphatase conjugate in phosphate buffered saline (PBS) buffer at 3 µg/ml;

(b) adding the solution of substep a. and reacting for 30 minutes at room temperature;

(c) washing with PBS buffer to remove unreacted material;

(d) adding a substrate of nitrophenyl phosphate to the reacted conjugate; and, (e) arresting the reaction after color develops with sodium hydroxide.

15. A method as described in claim 14 wherein the detecting of the concentration of the enzyme conjugate is by a microwell plate reader providing an indication of the optical density of the solution in the microwell.

16. A method as described in claim 15 wherein the microwell plate reader is calibrated to provide directly the quantity of oligonucleotide analyte present.

* * * * *